(12) United States Patent
Sasano et al.

(10) Patent No.: US 6,719,826 B2
(45) Date of Patent: Apr. 13, 2004

(54) METHOD AND APPARATUS FOR SAMPLE INJECTING IN GAS CHROMATOGRAPHY

(75) Inventors: Ryoichi Sasano, Wakayama (JP); Motoaki Satoh, Wakayama (JP); Yutaka Nakanishi, Wakayama (JP)

(73) Assignee: Saika Technological Institute Foundation, Wakayama (JP)

( * ) Notice: Subject to any disclaimer, the term of this patent is extended or adjusted under 35 U.S.C. 154(b) by 19 days.

(21) Appl. No.: 10/194,980

(22) Filed: Jul. 15, 2002

(65) Prior Publication Data

US 2004/0007129 A1 Jan. 15, 2004

(51) Int. Cl.⁷ .............................................. B01D 15/08
(52) U.S. Cl. .............................. 95/87; 73/23.41; 95/89; 96/102; 96/105
(58) Field of Search ..................... 73/23.35, 23.41; 95/82, 87, 89; 96/101, 102, 105

(56) References Cited

U.S. PATENT DOCUMENTS

| | | | | |
|---|---|---|---|---|
| 3,063,286 A | * | 11/1962 | Nerheim ..................... | 73/23.41 |
| 3,626,761 A | * | 12/1971 | Ferrin ........................ | 73/864.81 |
| 3,887,345 A | * | 6/1975 | Pollock et al. ............. | 96/105 |
| 4,035,168 A | * | 7/1977 | Jennings .................... | 73/864.85 |
| 4,474,588 A | * | 10/1984 | Hinshaw, Jr. .............. | 96/105 |
| 4,559,063 A | * | 12/1985 | Munari et al. ............. | 95/83 |
| 5,049,508 A | * | 9/1991 | Hilscher et al. ........... | 436/123 |
| 5,062,292 A | * | 11/1991 | Kanba et al. .............. | 73/19.01 |
| 5,252,109 A | * | 10/1993 | Munari et al. ............. | 95/87 |
| 5,347,844 A | * | 9/1994 | Grob et al. ................ | 73/23.41 |
| 5,686,656 A | * | 11/1997 | Amirav et al. ............ | 73/23.41 |
| 5,779,765 A | * | 7/1998 | Grob et al. ................ | 95/83 |
| 5,827,353 A | * | 10/1998 | O'Neil ....................... | 95/87 |
| 5,929,321 A | * | 7/1999 | Bertrand .................... | 73/23.39 |
| 5,954,862 A | * | 9/1999 | Wilson ....................... | 96/101 |
| 5,992,214 A | * | 11/1999 | Schlitt ....................... | 73/23.35 |
| 5,997,615 A | * | 12/1999 | Luong et al. .............. | 96/105 |
| 6,055,845 A | * | 5/2000 | Gerstel et al. ............. | 73/23.42 |
| 6,203,597 B1 | * | 3/2001 | Sasano et al. ............. | 95/87 |
| 6,423,120 B1 | * | 7/2002 | Nickerson et al. ........ | 95/87 |
| 6,494,939 B1 | * | 12/2002 | Tipler ........................ | 96/105 |
| 6,498,042 B1 | * | 12/2002 | Wilson ....................... | 436/174 |

* cited by examiner

Primary Examiner—Robert H. Spitzer
(74) Attorney, Agent, or Firm—Armstrong, Kratz, Quintos, Hanson & Brooks, LLP

(57) ABSTRACT

A method and an apparatus for sample injection in gas chromatography increases the injecting volume of a sample, and can analyze any of high-boiling-point compounds, low-compounds boiling-point compounds, and compounds decomposed by heat. A sample is injected into a vaporizing chamber 6 having curved or crooked outer wall 6G and sample path S and formed of continuous inner walls 6H; the sample is temporarily held in the vaporizing chamber 6; then an objective compound is vaporized, and introduced into a separation column 17.

17 Claims, 6 Drawing Sheets

METHOD AND APPARATUS FOR SAMPLE INJECTING IN GAS CHROMATOGRAPHY

BACKGROUND OF THE INVENTION

1. Field of the Invention

The present invention relates to a method and an apparatus for sample injection in gas chromatography.

2. Description of the Related Art

In a conventional apparatus for sample injection in gas chromatography, a vaporizing chamber is normally constituted from a thin, long, and straight glass tube whereto the needle of a syringe is inserted from the upper end, known as a liner, and is provided with a metal bottom plate member for closing the opening formed on the lower end of the glass tube and for inserting the end of the separation column.

When such a straight glass tube is used, the injected sample reaches the lower end of the vaporizing chamber instantly, and it takes a long time until the sample that has reached the bottom plate member positioned on the lower end of the vaporizing chamber is vaporized, and goes to the (upper) end of the separation column positioned above the bottom plate member. This may cause the detection data to change. Also, when the sample contacts the metal surface of the hot bottom plate, chemical change may occur, causing significant change in the detection data.

In order to prevent this, silica wool is generally packed in the vaporizing chamber so that the injected sample does not reach the lower end of the vaporizing chamber instantly.

In such a system, however, the objective compound may adhere to the silica wool, and may be retained or decomposed.

Since the conventional apparatus has a constitution in which a separation column is connected to the lower end of a straight vaporizing chamber, a large volume of sample cannot be held in the vaporizing chamber in a liquid state, and there is a problem of difficulty of large-volume injection because the normal injecting volume is 1 to 2 $\mu$l. Therefore, some large-volume injection systems with an increased injecting volume have been proposed. For example, in a system called on-column system, a pre-column is provided before a main column, a solvent in a sample is vaporized in the pre-column, and an objective compound is concentrated in the pre-column and transferred to the main column. In this system, however, a long pre-column is required, a solvent exhaust line must be provided, and the injection rate of the sample must be set accurately. In a system called baffle system, a solvent in a sample is vaporized on the surface of a baffle vaporizing chamber, an objective compound is concentrated on the surface of the vaporizing chamber and transferred to the column. However, this system is not suited for the analysis of low-boiling-point compounds, and a significant increase in injecting volume cannot be expected.

In view of the above-described situations, what the present invention is to solve is to provide a method and an apparatus for sample injection in gas chromatography that can significantly increase an injecting volume of a sample, and can analyze any of high-boiling-point compounds, low-boiling-point compounds, and compounds,decomposed by heat at a high accuracy.

SUMMARY OF THE INVENTION

The present invention can solve the above-described problems by using a method for sample injection in gas chromatography comprising the steps of injecting a sample through a curved or crooked sample path into a vaporizing chamber formed of continuous inner walls; temporarily holding the sample in a holding chamber provided in the vaporizing chamber; then vaporizing an objective compound; and introducing the objective compound into a separation column; or by using an apparatus for sample injection in gas chromatography comprising a vaporizing chamber, a syringe introducing portion installed above the vaporizing chamber, and a separation column connecting portion installed under the vaporizing chamber; in which the vaporizing chamber has a curved or crooked sample path and is formed with continuous inner walls, and comprises a holding chamber for temporarily holding the sample in the vaporizing chamber.

By using the vaporizing chamber having a curved or crooked sample path and formed with continuous inner walls as described above, the injected sample can be held temporarily in the vaporizing chamber, thus enabling the injection of a large volume of sample. By adjusting the temperature of the vaporizing chamber by supplying a heat medium such as heated air around the vaporizing chamber, the objective compound is vaporized, and the vaporized objective compound is introduced into the separation column for analysis.

By heating the sample held in the vaporizing chamber to first volatilize only the solvent and to discharge the volatilized solvent through a split vent; then adjusting the temperature in the vaporizing chamber to vaporize the objective compound; and introducing the objective compound into the separation column; the injecting volume can be increased, and the accuracy of the analysis can be improved as compared with the case where a sample is analyzed together with a solvent.

If the sample is easily decomposed by heat, by setting the initial temperature of the vaporizing chamber lower than the boiling point of the solvent in the sample; injecting the sample into the vaporizing chamber; slowly elevating the initial temperature of the vaporizing chamber to vaporize the objective compound; and introducing the objective compound into the separation column; even the sample easily decomposed by heat can be introduced into the separation column in a non-decomposed state.

If a large volume of the sample is injected, by setting the temperature of the vaporizing chamber lower than the boiling point of the solvent to maintain the injected sample in a liquid state in the holding chamber of the vaporizing chamber; discharging the volatilized solvent vapor through the split vent to concentrate the sample in the vaporizing chamber; then switching the mode to the splitless mode; and elevating the temperature of the vaporizing chamber to vaporize the objective compound: and introducing the objective compound into the separation column; the objective compound can be introduced into the separation column in the state where the physical change of the sample by an elevated temperature is avoided.

If the sample is derivatized for analyzing, by continuously injecting the sample and a derivatizing agent into the vaporizing chamber and holding in the holding chamber of the vaporizing chamber to derivatize the sample; and introducing the derivatized compound into the separation column; the analysis can be performed without touching the derivatizing agent.

By providing heating means and driving control means for controlling the drive of the heating means around the vaporizing chamber, the temperature in the vaporizing chamber can be maintained at the set temperature.

By constituting the heating means with an air chamber installed around the vaporizing chamber and a heated air delivery means for delivering heated air into the air chamber, the shape of the vaporizing chamber can be modified freely. In addition, compared with the constitution for heating with a conductive member made of a metal such as aluminum, any portions in the vaporizing chamber can be heated evenly and the cooling time can also be shortened.

The heated air delivery means may be constituted of a heater for warming the air, and a supply port installed on the wall surface forming the air chamber for supplying heated air warmed by the heater to the air chamber.

A needle of the syringe storing the sample penetrates the partition wall of the syringe introducing portion, and extends above the vaporizing chamber; and the syringe introducing portion comprises a carrier gas supply port and a septum purge vent.

The end of the separation column passes through the partition wall provided to the separation-column connecting portion, and extends below the vaporizing chamber.

A split vent is provided to the separation column connecting portion.

By constituting the vaporizing chamber from a single member, the number of members can be reduced comparing to the vaporizing chamber constituted by, for example, connecting two members.

DESCRIPTION OF SYMBOLS

Figure 1:
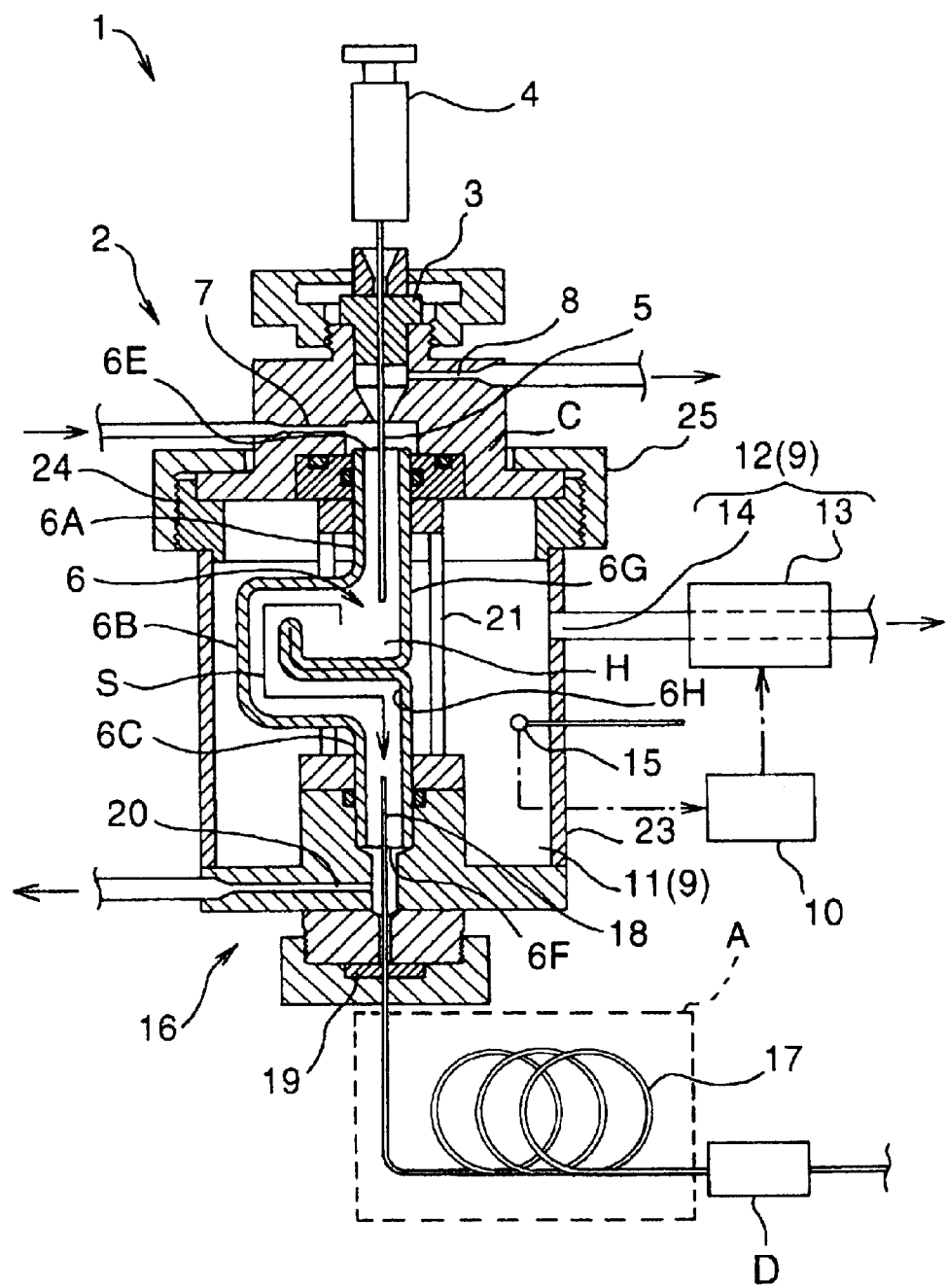
FIG. 1 is a sectional view showing an apparatus for sample injection of the present invention.

1 Injection apparatus
2 Syringe introducing portion
3 Septum
4 Syringe
5 Needle
6 Vaporizing chamber
6A Introduction tube portion
6B Guide tube portion
6C Up-down tube portion
6E, 6F Openings
6G Outer wall
6H Inner wall
7 Supply port
8 Vent
9 Heating means
10 Driving control means
11 Air chamber
12 Heated air delivery means
13 Heater
14 Supply port
15 Thermometer
16 Separation column connecting portion
17 Separation column
18 End
19 Graphite ferrule
20 Vent
21 Supporter
22 Vaporizing chamber
22A Introduction tube portion
22B Horizontal guide tube portion
22C Inclined tube portion
22D Up-down tube portion
22G Outer wall
22H Inner wall
23 Casing body
24 Threaded portion
25 Threaded member
26 Vaporizing chamber
26A Introduction tube portion
26B Horizontal guide tube portion
26C Up-down tube portion
26E, 26F Openings
26G Outer wall
26H Inner wall
27 Casing body
28 Heater
29 Insulator
30 Cover
31 Threaded member
32 Vaporizing chamber
32A Introduction tube portion
32B Vertical tube portion
32C Horizontal guide tube portion
32D Up-down tube portion
32G Outer wall
32H Inner wall
C Cover
D Detector
H Holding chamber

DETAILED DESCRIPTION OF THE PREFERRED EMBODIMENTS

FIG. 1 shows an apparatus for sample injection in gas chromatography (hereafter referred to as injection apparatus) 1 according to the present invention.

A syringe-introducing portion 2 is installed on the upper portion of the injection apparatus 1, and sealed with a septum 3, which is a partition wall made of a silicone-rubber-based material. The partition wall 3 may be made of any material such as metals and plastics as long as it can seal the partition wall 3. A sample is stored in the syringe 4 shown in FIG. 1. The needle 5 of the syringe 4 penetrates the septum 3, and extends to the upper portion of the vaporizing chamber 6. The sample stored in the syringe 4 passes through the needle 5, and injected into the vaporizing chamber 6. The syringe-introducing portion 2 is provided with a supply port 7 of a carrier gas, and a vent 8 of septum purge for separation and discharging.

As mentioned above, the liquid sample does not flow at once from the holding chamber H shown in FIG. 1, and therefore the holding chamber H is a liquid-holding chamber shaped to contain a liquid sample by gravity when the vaporizing chamber 6 is upright.

The vaporizing chamber 6 is made of a material such as glass and quartz (or may be made of a material such as ceramics, metals, or heat resistant plastics), and is an internal space formed of continuous inner walls 6H, and formed of a single hollow member (tube), whose outer walls 6G and inner walls 6H have a substantially same shape, and the middle portion in the length direction is crooked. The tube is also called the liner or insert. More specifically, there are provided an introduction tube portion 6A wherein the needle 5 is inserted, and having a holding chamber H formed for holding the sample injected from the needle 5; a guide tube portion 6B crooked to be substantially U-shaped from the introduction tube portion 6A; and an up-down tube portion 6C extending downwardly from the end of the guide tube portion 6B and wherein a part of the end portion 18 of the separation column 17, which will be described later, is inserted. Consequently, the injected sample is temporarily held in the holding chamber H, and does not flow to the lower portion of the vaporizing chamber 6 at once. Here, although the end portion 18 of the separation column 17 is inserted from the opening 6F for inserting in the separation column formed in the lower end of the up-down tube portion 6C of the vaporizing chamber 6, a through-hole can be formed at the location other than the lower end of the vaporizing chamber 6, for example, the sidewall of the up-down tube portion 6C, which is the lower portion of the vaporizing chamber 6, and the end portion 18 of the separation column 17 may be inserted through the through-hole.

Figure 7:
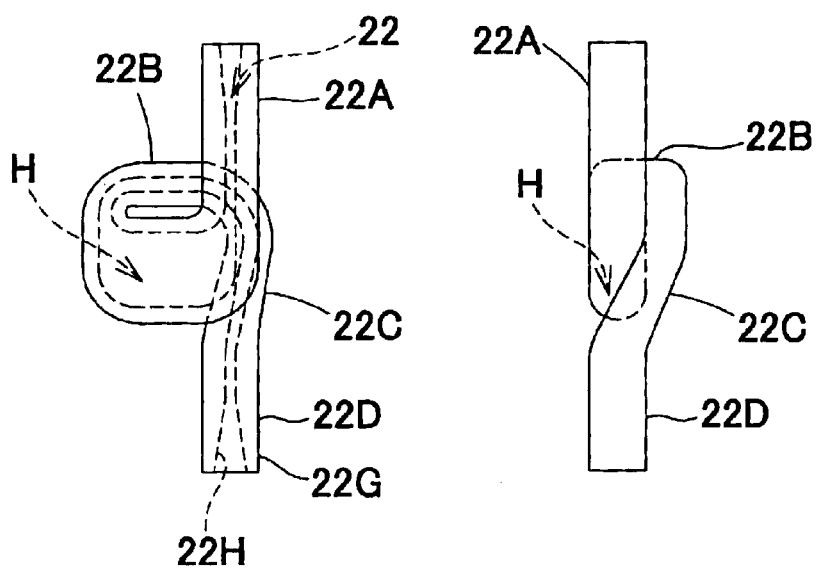
FIG. 7 shows other constitutions of the vaporizing chamber shown in FIG. 1; (a) being a front view thereof, and (b) being a side view thereof.

As the arrow in FIG. 1 shows, the sample path S of the injected sample from the needle 5 of the syringe 4 is a path, whose middle portion in the length direction is crooked crooked as inner and outer walls. Specifically, the injected sample is temporarily held in the holding chamber H of the introduction tube portion 6A, and after the objective compound vaporized from the holding chamber H has moved a little upward, it passes through the guide tube portion 6B formed in the U-shape and is swerved downward by the up-down tube portion 6C, and is guided to the end portion 18 of the separation column 17. In FIG. 1, by crooking the vaporizing chamber 6 in a small radius of curvature, increase in the size of the vaporizing chamber 6 can be avoided advantageously. However, the vaporizing chamber 6 may be curved in a large radius of curvature. Although the constitution of the vaporizing chamber 6 by the inner walls 6H and the outer walls 6G of substantially the same shape as described above has the advantage that any locations can be heated evenly by the heated air described later, the inner walls 22H may have a little different shape from the outer walls 22G as FIGS. 7(a) and (b) show. In FIGS. 7(a) and (b), although a part of the inner walls 22H has a little different shape from the outer walls 22G, these may be different entirely.

A heating means 9 and driving control means 10 for controlling the drive of the heating means 9 are provided around the vaporizing chamber 6, and the drive of the heating means 9 is controlled by the driving control means 10 so that the temperature of the vaporizing chamber 6 can be maintained to a temperature set by temperature setting means (not shown). The heating means 9 consists of an air chamber 11 installed around (outside) the vaporizing chamber 6, and heated air delivery means 12 for delivering heated air to the air chamber 11. The air delivery means 12 is composed of a heater 13 for heating the air, and a supply port 14 formed on the wall surface forming the air chamber 11 for supplying air heated by the heater 13. Therefore, air heated by the heater 13 is transferred to the air chamber 11, and the heated air controls the temperature in the vaporizing chamber 6. The temperature in the air chamber 11 is measured using a thermometer 15, the detected temperature from the thermometer 15 is inputted to the driving control means 10 to control the drive of the heater 13 and adjust the air heating volume to maintain the temperature in the vaporizing chamber 6 at the set temperature. By using the heated air, the temperature in the vaporizing chamber 6 can be adjusted evenly at any location in the vaporizing chamber 6 from a high temperature to a low temperature at a high accuracy.

Figure 8:
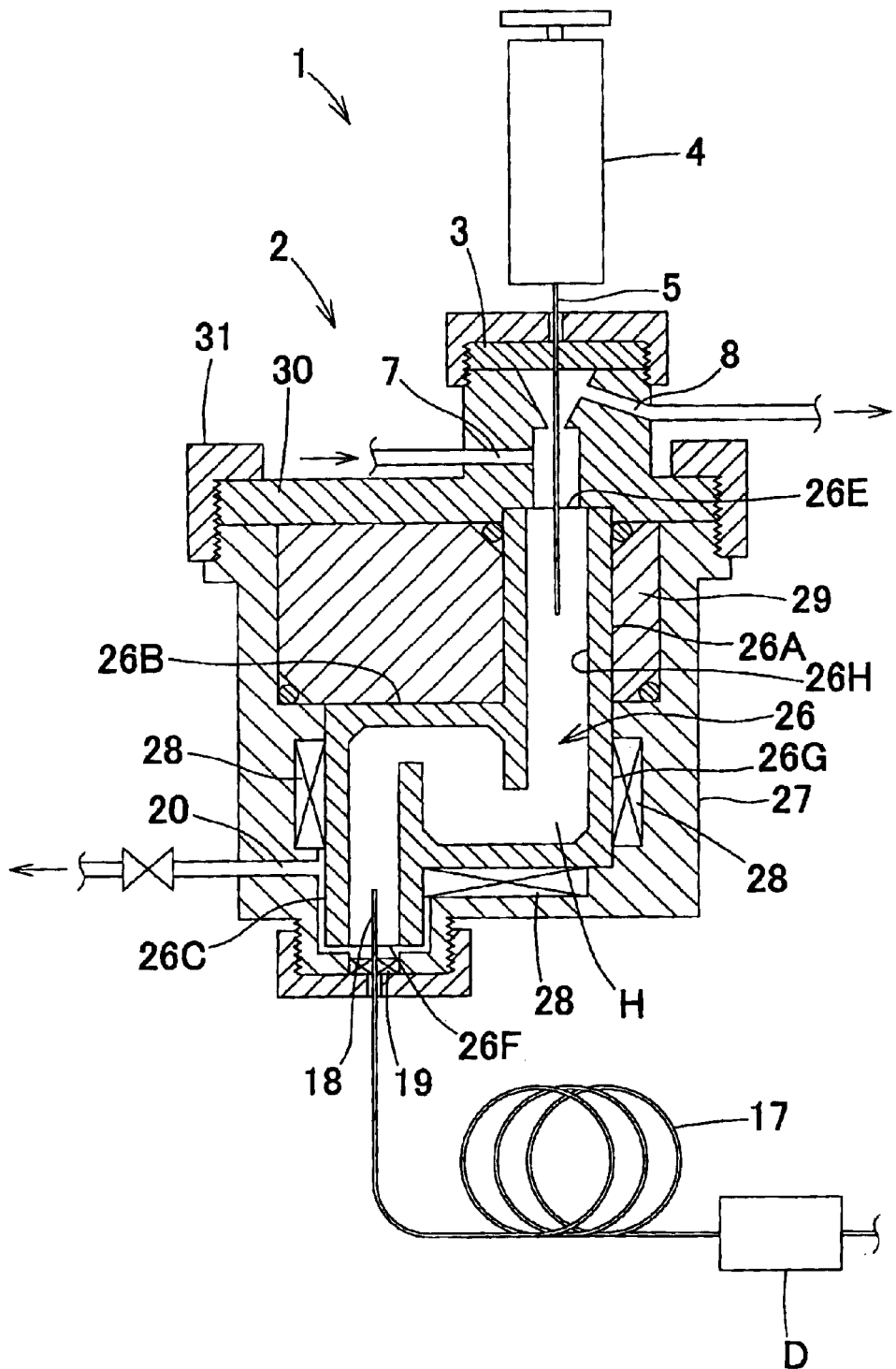
FIG. 8 is a sectional view showing an apparatus for sample injection of another constitution.

Although a suitable heat medium can be delivered to the air chamber 11 instead of heated air, and as FIG. 8 shows, the vaporizing chamber 26 can be heated indirectly by heating the casing body 27 composed of a metal such as aluminum for supporting the vaporizing chamber 26 with a plurality of heaters 28, this method required a large number of heaters 28. Also, the shape of the casing body 27 is not only limited by the shape of the vaporizing chamber 26, but also an insulator 29 and the like for filling the space inevitably formed for replacing the vaporizing chamber 26 from the casing body 27 is required. The cover 30 having a supply port 7 for the carrier gas and a vent 8 for septum purge is placed on the upper end of the casing body 27, and the cover 30 can be fixed to the casing body 27 by screwing a ring-shaped threaded member 31 integrated by screwing to the outer surface of the cover 30 in the threaded portion on the upper end of the casing body 27. When the vaporizing chamber 26 is replaced, after removing the threaded member 31, the cover 30, and the insulator 29, the vaporizing chamber 26 incorporated inside the casing body 27 is taken out, and a new vaporizing chamber 26 can be inserted. After replacing the vaporizing chamber 26, the insulator 29 and the cover 30 are placed, and the threaded member 31 is screwed.

Whereas in FIG. 1, only an air chamber 11 is formed in the casing body 23, and the vaporizing chamber 6 can be replaced only by removing the threaded member 25 screwed in the threaded portion 24 fixed on the upper end of the casing body 23. The symbol C shown in FIG. 1 denotes a cover 25 having a supply port 7 for the carrier gas and a vent 8 for septum purge, and for closing the opening of the threaded portion 24.

The lower portion of the injection apparatus 1 constitutes a separation-column connecting portion 16. The end 18 of the separation column 17 passes through a graphite ferrule 26, which is a partition wall, and extends into the vaporizing chamber 6. The separation-column connecting portion 16 is provided with a vent 20 of the split for separating and discharging. The partition wall 26 is made of any materials such as rubber, plastics, or metals as long as it can be used for sealing.

The vaporizing chamber 6 is upright installed in the injection apparatus 1 with the help of a supporter 21. Since both the upper and lower ends of the vaporizing chamber 6 are situated on the same straight line, it is convenient to install and remove, and easily supported upright. FIGS. 7(a) and (b) show a vaporizing chamber 22 of another embodiment. The vaporizing chamber 22 consists of an introduction tube portion 22A for receiving the sample injected from the needle 5; a horizontal guide tube portion 22B extending from the upper end of the holding chamber H formed in the lower portion of the introduction tube portion 15A so that the upper portion of the holding chamber H is horizontally detoured; an inclined tube portion 22C directing from the end of the horizontal guide tube portion 22B obliquely downward; and an up-down tube portion 22D guiding the sample from the lower end of the inclined tube portion 22C downward. The shape of the vaporizing chamber is optional.

The upper and lower ends of the vaporizing chamber 22 in FIGS. 7(a) and (b) are also situated on the same straight line. Although the constitution of FIGS. 7(a) and (b) is to deliver the sample injected from the above to the end 18 of the underlying separation column 17, the end 18 may be placed horizontally to receive the sample horizontally.

Next, a method for injecting a sample will ,be described referring to FIG. 1. The sample held in the syringe 4 is injected through a needle 5 into a vaporizing chamber 6.

There is an expanded holding chamber H in the vaporizing chamber 6, and the injected sample is temporarily held in the holding chamber H. Therefore, there is no need to fill the vaporizing chamber 6 with silica wool and the like in order to prevent the sample from flowing to the lower portion of the vaporizing chamber 6 at once. Then, heated air is transferred to the air chamber 11 to heat the air chamber 11 to vaporize the objective compound, the objective compound is transferred to the separation column 17 from the bottom of the vaporizing chamber 6, and the compound is analyzed with the detector D. When the sample is injected, a carrier gas such as helium can be transferred from the carrier gas supply port 7, or the vent 8 of the septum purge can be opened for separating and discharging. Also during heating, the split mode can be switched to the splitless mode by opening and closing the vent 20 of the split. Therefore, both a high-boiling-point compound and a low-boiling-point compound can be analyzed accurately by setting these conditions. The split mode means the state where the vent 20 of the split is opened so as to separate and discharge the sample injected from the vent 20, and the splitless mode means the state where the vent 20 of the split is closed so as not to separate and discharge the sample.

Although the injection method is briefly described above, further details will be described for each type of analysis. In the case of the sample that is easily decomposed by heat during analysis, the analysis is performed in the cold splitless system. Specifically, the temperature in the vaporizing chamber 6 is set to a temperature lower than the boiling point of the sample solvent, the mode is set to the splitless mode, and the sample is injected into the vaporizing chamber 6. The sample is temporarily held in the holding chamber H. Then, heated air is transferred to the air chamber 11, and the temperature in the vaporizing chamber 6 is slowly elevated to vaporize the objective compound to introduce the vaporized objective compound into the separation column 17. Finally, the mode is switched to the split mode, the temperature in the vaporizing chamber 6 is further elevated to vaporize the solvent and foreign matter remaining in the vaporizing chamber 6, and to discharge them from the vent 20 of the split. Thereby, the degradation of the separation column 17 can be prevented.

An example of analytical test in the cold splitless system will be described below.

The sample was prepared from an agricultural chemical (trichlorfon), which is easily decomposed by heat during analysis, whereto n-C14 was added as an internal standard compound, and diluted by acetone. The conditions of analysis were as follows:

Column: DB-5 ms, 0.25 mm i.d.×30 m, df=0.25 $\mu$m

Vaporizing chamber temperature: 50° C.–25° C./min–150° C. (2 min)

Oven temperature: 50° C. (5 min)–20° C./min–24° C. (4 min)

Carrier gas: He

Split initial flow rate: 30 ml/min

Splitless time: 5 min

Injecting volume: 2 $\mu$l

Figure 2:
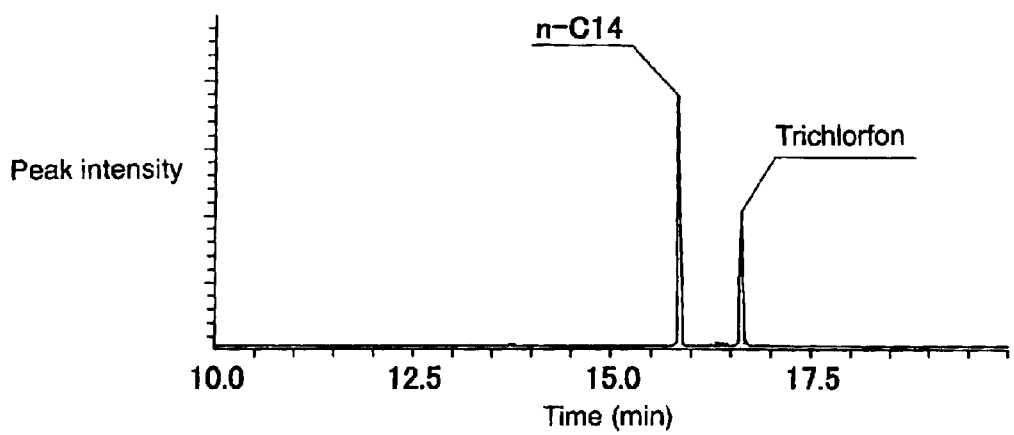
FIG. 2 is a chromatogram obtained using the cold splitless injection method.

The chromatogram obtained by the above-described analytical test is shown in FIG. 2. Since the initial temperature in the vaporizing chamber 6 was 50° C., the objective compound was not decomposed by heat, and a good chromatogram could be obtained. According to a conventional method, since the temperature in the vaporizing chamber is normally 260° C., the objective compound is decomposed by heat, and a good chromatogram cannot be obtained.

Next, the case where a large volume of the sample is injected and analyzed will be described referring to FIG. 3. In this case, the temperature in the vaporizing chamber 6 is set to be lower than the boiling point of the solvent so that the solvent of the injected sample is not boiled, and the sample is injected from the syringe 4 into the vaporizing chamber 6, and the sample is held in the holding chamber H in a liquid state. The mode is set to the split mode, and the volatilized solvent vapor is discharged from the vent 20 of the split to concentrate the sample in the vaporizing chamber 6.

Next, the mode is switched to the splitless mode, heated air is transferred into the air chamber 11 to slowly elevate the temperature in the vaporizing chamber 6 and to vaporize the objective compound, and the vaporized objective compound is introduced into the separation column 17. Finally, the mode is switched to the split mode again, the temperature in the vaporizing chamber 6 is further elevated to vaporize the foreign matter remaining in the vaporizing chamber 6, and the vaporized foreign matter is discharged from the vent 20 of the split. FIG. 3 shows a graph of the injection port temperatures, which are the temperatures in the vaporizing chamber 6 measured using a thermometer or the like; and the column oven temperatures, which are the temperatures of the separation column 17 surrounded by the broken lines A in FIG. 1 using a thermometer or the like.

When the sample is concentrated in the vaporizing chamber 6, low-boiling-point compounds are also discharged from the vent 20 of the split. In order to solve this problem, for example, an adsorbing agent may be packed in the vaporizing chamber 6 between the holding chamber H and the vent 20 of the split to adsorb the low-boiling-point compounds discharged from the vent 20 of the split, and the temperature in the vaporizing chamber 6 may be elevated slowly to ensure that the low-boiling-point compounds held by the adsorbing agent is introduced into the separation column 17. The adsorbing agent may also be disposed in the holding chamber H, or an adsorbing agent or a special liquid for holding low-boiling-point compounds may be applied to the inner walls 6H of the vaporizing chamber 6.

An example of analytical test in the case of a large volume injection will be described.

The samples were prepared from agricultural chemicals (bendiocarb, carbaryl, methiocarb), which are easily decomposed by heat during analysis, whereto n-C20 was added as an internal standard compound, and diluted by acetone. The conditions of analysis were as follows:

Column: DB-5 ms, 0.25 mm i.d.×30 m. df=0.25 $\mu$m

Vaporizing chamber temperature: 50° C.–30° C./min–180° C. (2 min)

Oven temperature: 50° C. (5 min)–20° C./min–240° C. (4 min)

Carrier gas: He

Split initial flow rate: 30 ml/min

Splitless time: 5 min

Injecting volume: 100 $\mu$l

Figure 3:
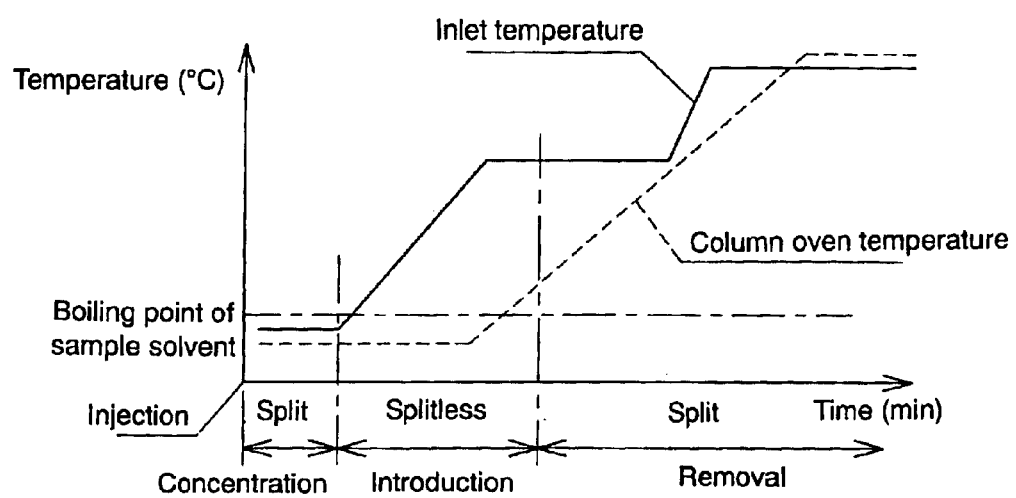
FIG. 3 is a diagram showing conditions when a large volume of the sample is injected.
Figure 4:
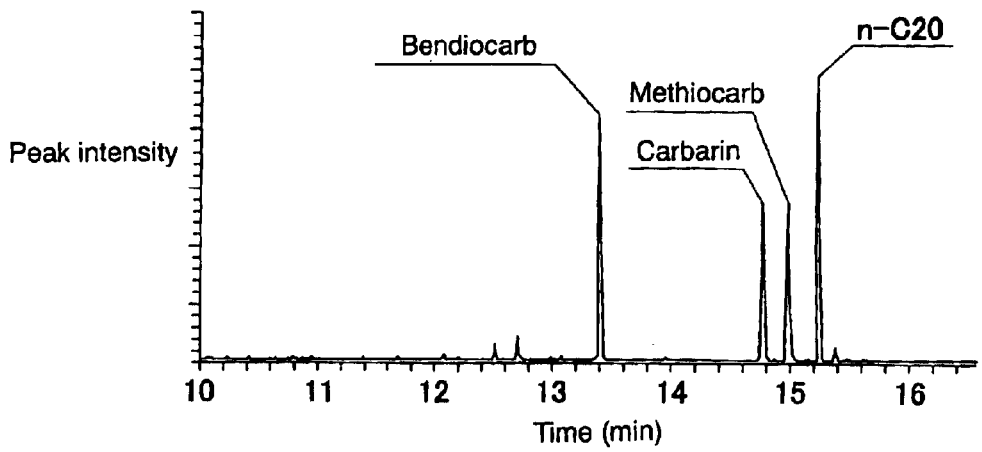
FIG. 4 is a chromatogram obtained using the large-volume sample injection method.

The outline of the conditions for the above-described analytical test is shown in FIG. 3. The chromatogram obtained by the analytical test is shown in FIG. 4. A good chromatogram with fine peak shapes was obtained. Although the samples were compounds easily decomposed by heat during analysis, no decomposition by heat occurred as shown in FIG. 4. Since the injecting volume, which was conventionally 1 to 2 μl, can be increased to about 100 μl, and the sensitivity in analysis can be raised to 50 to 100 times, the pre-concentration treatment for sample preparation becomes simplified, and the speed of the pretreatment can be increased and the labors and costs can be saved.

An example of the accuracy test for an analysis with large volume injection will be described.

Figure 5:
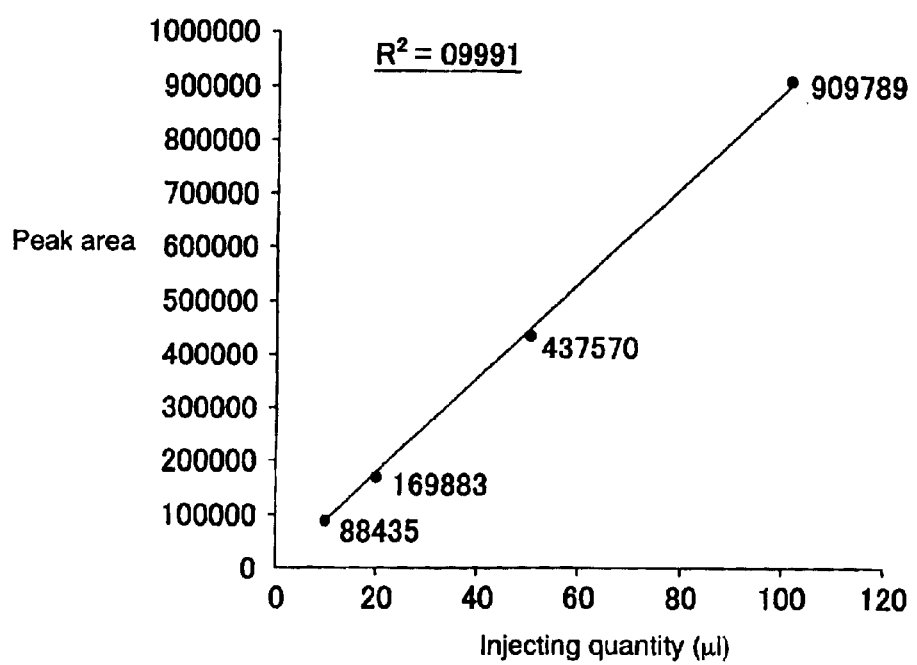
FIG. 5 is a diagram showing the accuracy of the large-volume sample injection method.

In order to measure the accuracy when a large volume injection is used, the relationship between the injecting volume (10, 20, and 100 μl) and the response (peak area and height) was obtained. The relative standard deviation when the injection of 50 μl was repeated for 7 times was also obtained. The sample was prepared by diluting a hydrocarbon n-C16 with acetone. The conditions of analysis were as follows:

Column: DB-5 ms, 0.25 mm i.d.×30 m, df=0.25 μm
Vaporizing chamber temperature: 50° C.–30°m C./min–180° C. (2 min)
Oven temperature: 50° C. (5 min)–20° C./min–240° C. (4 min)
Carrier gas: He
Split initial flow rate: 30 μl/min
Splitless time: 5 min A graph showing the relationship between the flow rate and the response is shown in FIG. 5. An obvious straight relationship was obtained between the injecting volume and the response. The relative standard deviation of the repeated tests was 1.92 (%). These straightness and repeatability proved a high accuracy of analysis using the large-volume injecting method.

An example of the analytical test using the derivatization injecting method will be described.

Figure 6:
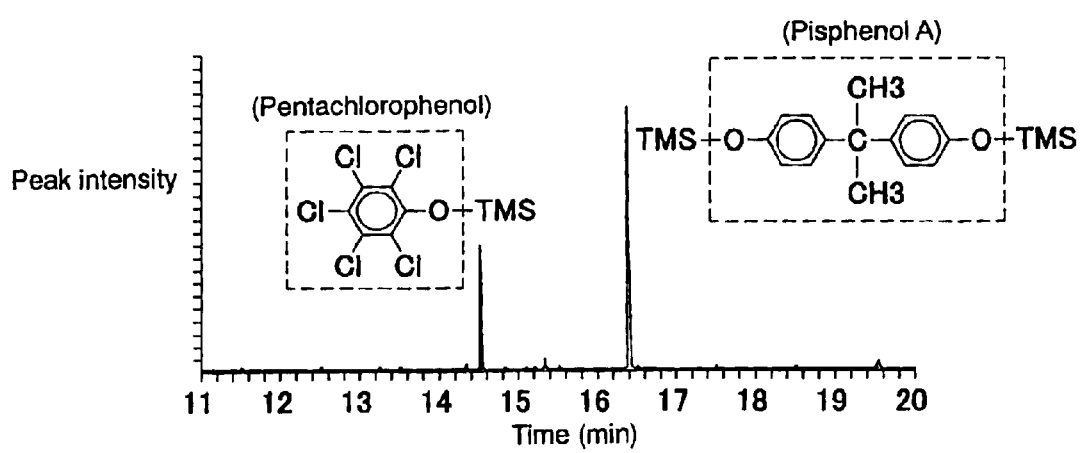
FIG. 6 is a chromatogram obtained using the sample derivatization method.

An analytical test wherein a sample and a derivatizating agent were sequentially injected, and derivatized in the vaporizing chamber was performed. As the sample, pentachlorophenol and bisphenol A diluted with acetone were used. As the derivatizating reagent, BSTFA (N, 0-Bis (trimethylsilyl) trifluoroacetamide) diluted with acetone was used. The conditions of analysis were as follows:

Column: DB-5ms, 0.25 mm i.d.×30 m, df=0.25 μm
Vaporizing chamber temperature: 50° C.–30° C./min–180° C. (2 min)
Oven temperature: 50° C. (5 min)–20° C./min–240° C. (4 min)
Carrier gas: He
Split initial flow rate: 30 ml/min
Splitless time: 5 min
Sample injecting volume: 2 μl
BSTFA injecting volume: 1 μl The procedures of this analytical test are as follows: A sample is injected and held in the holding chamber H on the vaporizing chamber 6. Next, the derivatizating reagent (BSTFA) is injected into the vaporizing chamber 6. The temperature in the vaporizing chamber 6 is set to a suitable temperature to derivatize the sample while concentrating. The derivative compound is introduced into the separation column 17. The chromatogram of this analysis is shown in FIG. 6. The results showed that the derivatization was surely performed. The use of the derivatization method can save the pretreatment for previous derivatizing, can derivatize the sample without touching the derivatizating reagent, which may adversely affect human bodies, and has the advantage that analysis can be performed immediately after derivatization.

Although an opening 6E for injecting the sample on the upper end of the vaporizing chamber 6 and an opening 6F for inserting the separation column on the lower end of the vaporizing chamber 6 are placed so as to align in the up-down direction in FIG. 1, the opening 26E for injecting the sample on the upper end of the vaporizing chamber 6 and an opening 26F for inserting the separation column on the lower end of the vaporizing chamber 6 may be placed on the different locations in the up-down direction as shown in FIG. 8. The vaporizing chamber 26 shown in FIG. 8 consists of an introduction tube portion 26A having an inner wall 26H and an outer wall 26G constituted in a crooked shape at the middle portion in the length direction, and for inserting the needle 5 of a syringe 4; a horizontal guide tube portion 26B horizontally extending from the upper end of the holding chamber H formed under the introduction tube portion 26A; and an up-down tube portion 26C downwardly extending from the end of the horizontal guide tube portion 22B. Since other features that have not been described but are shown in FIG. 8 are functionally the same as features shown in FIG. 1, (although the shapes are a little different), they are denoted by the same symbols as in FIG. 1.

Figure 9:
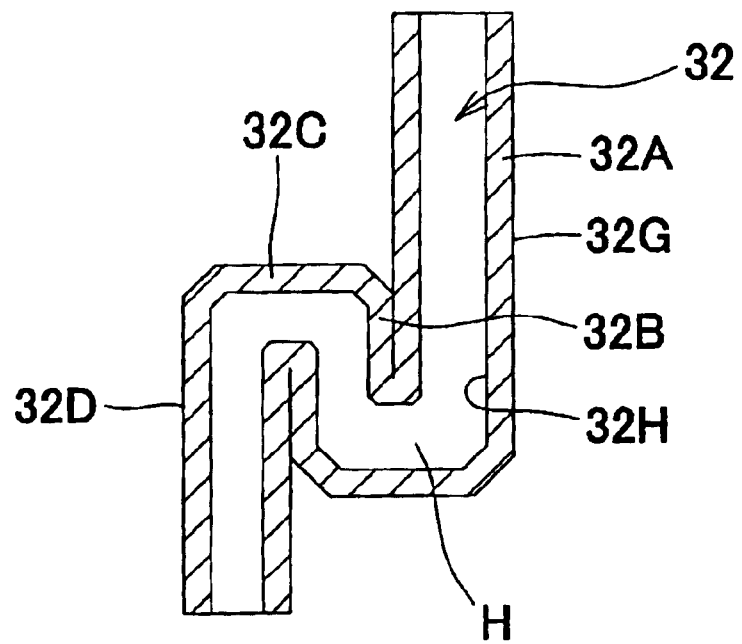
FIG. 9 shows other constitutions of the vaporizing chamber shown in FIG. 8.

Alternatively, the vaporizing chamber 26 shown in FIG. 8 may be constituted as FIG. 9 shows. In FIG. 9, the vaporizing chamber 32 is formed by bending a glass tube, different from the integrally formed vaporizing chamber 26 shown in FIG. 8. The vaporizing chamber 32 shown in FIG. 9 consists of an introduction tube portion 32A having an inner wall 26H and an outer wall 26G constituted in a crooked shape at the middle portion in the length direction, and for inserting the needle 5 of a syringe 4; a vertical tube portion 32B rising upwardly from the end of the holding chamber H formed under the introduction tube portion 32A; a horizontal guide tube portion 32C horizontally extending from the upper end of the vertical tube portion 32B; and an up-down tube portion 32D downwardly extending from the end of the horizontal guide tube portion 32B.

Since the sample injected by the method of the present invention is temporarily held in the vaporizing chamber, the sample can be analyzed stably at a high accuracy. In other words, the sample is not decomposed by contacting the metal surface on the lower end of the vaporizing chamber as in a conventional method, and the retention of the objective compound adhered to silica wool, which is caused by filling the vaporizing chamber with silica wool, can be prevented. Since the temperature in the vaporizing chamber is adjusted with heated air or the like, the temperature can be adjusted quickly at a high accuracy to ensure that the objective compound is vaporized and introduced into the separation column.

As described above, according to the injection method of the present invention, the compounds of both high-boiling-point compounds and low-boiling-point compounds can be analyzed accurately by suitably setting analyzing conditions. Furthermore, by setting the initial temperature of the vaporizing chamber, and vaporizing the objective compound in the splitless mode, even compounds that are easily decomposed by heat can be analyzed without thermal decomposition. Also, by injecting a large volume of the sample into the vaporizing chamber and concentrating the sample in the split mode, the sensitivity of the analysis can be improved, and the pretreatment of the sample can be simplified. Furthermore, since the sample and the derivatizing agent can be injected sequentially into the vaporizing chamber to derivatize the sample in the vaporizing chamber, there is an advantage that the analysis can be performed without touching the derivatizing agent, and immediately after derivatization.

The injection apparatus of the present invention can be manufactured by only a simple modification to the constitution for holding the sample in the vaporizing chamber, can be manufactured and assembled easily, and can be manufactured and provided at low costs.

What is claimed is:

1. A method for sample injection in gas chromatography comprising the steps of:
    providing a vaporizing chamber further comprising (1) continuous inner walls, (2) a curved or crooked sample path, and (3) a liquid-holding chamber shaped to contain a liquid sample by gravity when the vaporizing chamber is upright;
    injecting the sample into the liquid-holding chamber;
    temporarily holding the sample in the liquid-holding chamber provided in said vaporizing chamber;
    vaporizing an objective compound of the liquid sample in the liquid-holding chamber; and
    introducing the objective compound into a separation column.

2. The method for sample injection in gas chromatography according to claim 1, wherein said sample held in said holding chamber is heated to first volatilize only a solvent and to discharge a volatilized solvent through a split vent; then the temperature in said vaporizing chamber is adjusted to vaporize the objective compound; and the objective compound is introduced into said separation column.

3. The method for sample injection in gas chromatography according to claim 1, wherein the initial temperature of said vaporizing chamber is set lower than the boiling point of a solvent in the sample; the sample is injected into the vaporizing chamber; the initial temperature of said vaporizing chamber is slowly elevated to vaporize the objective compound; and the objective compound is introduced into said separation column.

4. The method for sample injection in gas chromatography according to claim 3, wherein the sample is heat decomposable sample.

5. The method for sample injection in gas chromatography according to claim 1, wherein the temperature of said vaporizing chamber is set lower than the boiling point of a solvent to maintain the injected sample in a liquid state in the holding chamber of said vaporizing chamber; volatilized solvent vapor is discharged through a split vent to concentrate the sample in said vaporizing chamber; then a mode is switched to a splitless mode; and the temperature of said vaporizing chamber is elevated to vaporize the objective compound; and the objective compound is introduced into said separation column.

6. The method for sample injection in gas chromatography according to claim 5, wherein a large volume of the sample is injected.

7. The method for sample injection in gas chromatography according to claim 1, wherein the sample is derivatized for analyzing, the sample and a derivatizing agent are continuously injected into said vaporizing chamber and held in the holding chamber of said vaporizing chamber to derivatize the sample; and the derivatized compound is introduced into said separation column.

8. The method for sample injection in gas chromatography according to any of claims 1 to 7, wherein said vaporizing chamber is constituted of a single member.

9. An apparatus for sample injection in gas chromatography comprising a vaporizing chamber, a syringe introducing portion installed above the vaporizing chamber, and a separation column connecting portion installed under said vaporizing chamber; wherein said vaporizing chamber has a curved or crooked sample path and is formed with continuous inner walls and comprises holding chamber for temporarily holding the sample in said vaporizing chamber.

10. The apparatus for sample injection in gas chromatography according to claim 9, wherein heating means and driving control means for controlling the drive of said heating means are provided around said vaporizing chamber.

11. The apparatus for sample injection in gas chromatography according to claim 10, wherein said heating means comprises an air chamber installed around said vaporizing chamber, and heated air delivery means for delivering heated air into said air chamber.

12. The apparatus for sample injection in gas chromatography according to claim 11, wherein said heated air delivery means comprises a heater for warming the air, and a supply port installed on the wall surface forming said air chamber for supplying air heated by said heater to said air chamber.

13. The apparatus for sample injection in gas chromatography according to claim 9, wherein a needle of the syringe storing the sample penetrates the partition wall of said syringe introducing portion and extends above said vaporizing chamber; and said syringe introducing portion comprises a carrier gas supply port and a septum purge vent.

14. The apparatus for sample injection in gas chromatography according to claim 9, wherein the end of said separation column passes through the partition wall provided to the separation column connecting portion, and extends below said vaporizing chamber.

15. The apparatus for sample injection in gas chromatography according to claim 14, wherein a split vent is provided to said separation column connecting portion.

16. The apparatus for sample injection in gas chromatography according to claim 9, wherein a split vent is provided to said separation column connecting portion.

17. The apparatus for example injection in gas chromatography according to any one of claim 9 to 15, wherein said vaporizing chamber is constituted from a single member.

* * * * *